Figure 1:
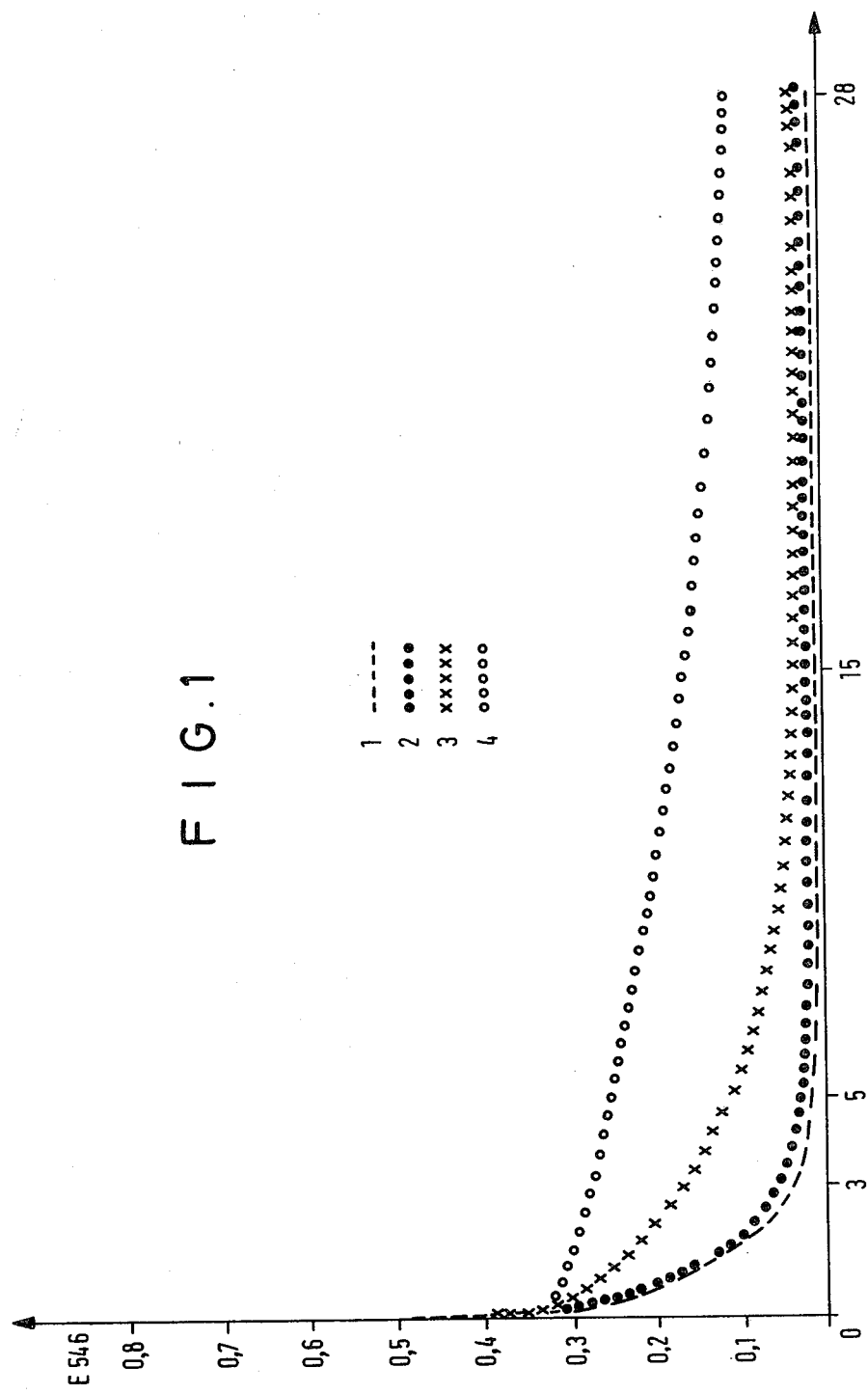

United States Patent [19]

Batz et al.

[11] 4,378,227

[45] Mar. 29, 1983

[54] PROCESS AND REAGENT FOR DISSOLVING CHYLOMICRONS IN AQUEOUS MATERIAL

[75] Inventors: Hans-Georg Batz, Tutzing; Siegfried Looser, Weilheim, both of Fed. Rep. of Germany

[73] Assignee: Boehringer Mannheim GmbH, Mannheim-Waldhof, Fed. Rep. of Germany

[21] Appl. No.: 265,525

[22] Filed: May 20, 1981

[30] Foreign Application Priority Data

Jun. 6, 1980 [DE] Fed. Rep. of Germany ....... 3021457

[51] Int. Cl.$^3$ .................... G01N 33/52; G01N 33/92
[52] U.S. Cl. .................... 436/17; 23/293 R; 23/909; 252/173; 252/554; 435/4; 435/11; 435/15; 435/25; 436/71
[58] Field of Search .................... 252/408, 173, 554; 23/230 B, 909, 293 R; 435/4, 7, 11, 15, 25

[56] References Cited

U.S. PATENT DOCUMENTS

| | | | |
|---|---|---|---|
| 4,011,045 | 5/1977 | Bonderman | 23/230 B |
| 4,153,570 | 5/1979 | Hennemann et al. | 252/554 X |
| 4,184,848 | 1/1980 | Batz et al. | 23/230 B |
| 4,226,713 | 10/1980 | Goldberg | 23/230 B |
| 4,282,001 | 8/1981 | Klose et al. | 23/909 X |
| 4,289,649 | 9/1981 | Harders et al. | 23/230 B X |

*Primary Examiner*—Arnold Turk
*Attorney, Agent, or Firm*—Felfe & Lynch

[57] ABSTRACT

A process for dissolving chylomicrons in an aqueous medium composed of (a) at least one polyethylene glycol ether of an alkanol or alkylaryl alcohol with a branched alkane chain and with an HLB value of 12 to 14, and (b) at least one secondary alkyl sulphonate containing 10 to 20 carbon atoms in the molecule, and optionally (c) an alkali metal p-toluenesulphonate; and the agent formed by the combination of (a), (b) and optionally (c).

15 Claims, 2 Drawing Figures

PROCESS AND REAGENT FOR DISSOLVING CHYLOMICRONS IN AQUEOUS MATERIAL

This invention relates to a process and an agent for dissolving chylomicrons in aqueous media, such as turbid sera, using a surface-active polyethylene glycol derivative.

Chylomicrons are fine particles which, to an extent of more than 90%, consist of lipids and cholesterol and have a covering of lipoproteins. They occur in biological materials, especially in blood and serum. Sera rendered turbid by such chylomicrons are particularly obtained when blood is sampled for obtaining serum after a fat-rich meal or in the case of certain diseased conditions. Such sera rendered turbid by chylomicrons cannot be used for carrying out determinations by photometric measurements.

The chylomicron fractions also serve as starting material for obtaining substances contained therein. In this case, too, it is necessary to dissolve the chylomicrons in an aqueous medium in order that the components can be obtained under mild conditions and a homogeneous reaction can be carried out.

Combinations of lipids, phospholipids and lipoproteins also occur in cell membranes but with different percentage compositions. A series of detergents is already known which are able to dissolve such cell membranes. Non-anionic tensides which are ethers of polyethylene glycol with n-alkanols or with alkylphenols are especially suitable for this purpose but these tensides are not able to dissolve chylomicrons.

From Federal Republic of Germany Patent Specification No. 23 27 894 it is already known to clarify turbidities with polyethylene glycol esters of laurates which have a particular composition and thus a particular HLB value. However, an important disadvantage of the laurate esters is that the ester bond is split by lipases and esterases which are frequently present in biological material together with the chylomicrons so that their usefulness for dissolving chylomicrons is limited.

It is also known, in the scope of a method for the determination of iron, to dissolve chylomicrons, which disturb this determination, by the addition of a surface-active agent containing secondary alkyl sulphates (see Z. Klin. Chem., 3, 96–99/1965). On the other hand, however, primary alkyl sulphates, such as sodium dodecyl sulphate, prove to be useless for the dissolving. And, this agent is no longer commercially available.

Consequently, there is a need for a process and an agent which is able to dissolve chylomicrons in aqueous media. In particular, there is a need for such a process and agent with the use of which the clarification takes place quickly and completely and is concluded after at most 3 to 5 minutes.

It is an object of the present invention to satisfy this need.

DESCRIPTION

Thus, according to the present invention, there is provided a process for dissolving chylomicrons in an aqueous medium by adding a surface-active polyethylene glycol derivative, wherein there is added to the aqueous medium:

(a) at least one polyethylene glycol ether of an alkanol or alkylaryl alcohol with a branched alkane chain and with an HLB value of 12 to 14, and (b) at least one secondary alkyl sulphonate containing 10 to 20 carbon atoms in the molecule, and optionally (c) an alkali metal p-toluenesulphonate.

Particularly good results are obtained when a polyethylene glycol ether of the branched-chained alkanol and the alkyl sulphonate(s) are used in a ratio of 8 to 4 parts by weight of polyethylene glycol ether and 2 to 6 parts by weight of alkyl sulphonate.

Since, due to the addition of the branch-chained polyethylene glycol ether and of the alkyl sulphonate, a considerable increase of the viscosity of the aqueous medium can take place, in many cases it is advisable also to add an alkali metal toluenesulphonate, preferably the sodium salt, for lowering the viscosity. The amount added depends upon the desired reduction of viscosity and upon the initial viscosity of the aqueous medium which contains the branched-chained polyethylene glycol ether and alkyl sulphonate. In general, a sufficient reduction of viscosity is obtained with additions of 5 to 10% by weight, referred to the sum of the two above-mentioned additives. The branched-chained polyethylene glycol ether used is preferably one with an HLB value of from about 12.5 to about 13.5. The HLB value[1] range of 12 to 14 or the preferred range of 12.5 to 13.5 would, in the case of polyethylene glycol ethers of straight-chained alkanols and arylalkanols, correspond to an average of 7 to 12 and preferably of 8 to 10 polyethylene oxide units. In the case of the branched-chained alkanol ethers, these values are displaced somewhat but not substantially. Since the technical grade polyethylene glycol ethers are always present as mixtures with differing chain lengths of the polyethylene glycol part of the molecule, the above-given numerical values only signify average values. However, the chain length distribution is to have maximum values within the above-given chain lengths. The determination of HLB values is described, for example, by H. Stache in "Tensid-Taschenbuch", pub. Carl Hanser-Verlag, Munchen, Wien, pp. 70–72, 1979.

[1] The HLB value (hydrophile-lipophile-balance) is calculated from the hydrophilic and hydrophobic structure-elements of a tenside molecule.

Typical examples of polyethylene glycol ethers of alkylaryl alcohols with branched alkane chains which can be used according to the present invention include the ethers of tert.-octylphenol, of isooctylphenol, of isononylphenol, of isodecylphenol, etc. The alkanol or alkylaryl alcohol residue can contain 4 to about 20 carbon atoms. If it contains an aryl radical and preferably a phenyl radical, the branched alkyl chain should contain at least 7 carbon atoms. Amongst the ethers which do not contain aryl radicals, there may, for example, be mentioned those of isooctanol, isononanol, isodecanol, isoundecanol, isododecanol, isotridecanol and isotetradecanol, etc. up to 16 carbon atoms. The branched-chained alkanols containing 12 to 14 carbon atoms are preferably used. Amongst the preferred isotridecanols, there may, for example, be mentioned trimethyldecanol, tetramethylnonanol and pentamethyloctanol. The amount added is preferably from 1 to 10 and more preferably from 3 to 6% by volume of the total batch.

Amongst the alkane sulphonates, in general there are suitable the secondary alkyl- mono- and di-sulphonates containing 10 to 20 carbon atoms in the molecule, those with 13 to 15 carbon atoms in the molecule being preferred. Use can be made not only of pure compounds but also of mixtures. It is preferred to use mixtures of secondary alkyl- mono- and di-sulphonates containing up to 50% of disulphonated compounds. Suitable mixtures are commercially available, for example, under the trade name "Mersolate".[2] The amount of alkane sulphonate added is preferably from 3 to 20 and more preferably from 4 to 8% by volume of the total batch.

[2] Bayer

The process according to the present invention can be carried out by successively adding the individual components. However, it is preferable to use a premixture of the branched-chained polyethylene glycol ethers and of the alkyl sulphonates, which can also already contain an alkali metal toluenesulphonate, this premixture being added to an aqueous medium containing chylomicrons in an amount which results in a dissolving of the chylomicrons in a short period of time. The dissolving time should be less than 5 and preferably less than 3 minutes. By means of a preliminary experiment, it is possible, in each case, rapidly to ascertain the amount of dissolving additives necessary. In general, in the case of turbid sera, this amount is from about 4 to about 30% by volume. If the dissolving of the chylomicrons is carried out for preparative purposes, then the speed of dissolving is not an important factor so that the smallest possible amount will be added in order not to entrain unnecessarily large amounts of impurities.

The quickest possible dissolving of the chylomicrons is of particular importance when the process of the present invention is employed within the scope of the determination of serum components using automatic analyzers. In this case, due to the construction of the automatic devices, the times are usually predetermined within which dissolving must take place and, especially in the case of high capacity automatic devices, these times are very short and are frequently less than one minute. With the process according to the present invention, it is possible, even in such cases, to fulfil the predetermined time conditions.

The present invention also provides an agent for dissolving chylomicrons in aqueous media which contains surface-active polyethylene glcyol derivatives, wherein it contains (a) at least one polyethylene glycol ether of an alkanol or arylalkanol with a branched alkane chain and an HLB value of 12 to 14, and (b) at least one secondary alkyl sulphonate containing 10 to 20 carbon atoms in the molecule, and optionally (c) an alkali metal p-toluenesulphonate.

The agent preferably contains 8 to 4 parts by weight of polyethylene glycol ether to 2 to 6 parts by weight of alkane sulphonate, as well as possibly 5 to 10% by weight of alkali metal toluenesulphonate, referred to the sum of the two above-mentioned essential components. The statements made above with regard to the process apply in the same way to the general and the preferred range of the HLB value or to the chain length of the polyethylene glycol. This also applies to the alkyl sulphonates.

The technical effects which can be achieved with the process and agent according to the present invention are surprising since the primary and secondary alkyl sulphonates alone show no dissolving action for chylomicrons whatsoever and the polyethylene glycol ethers of the branched-chained alkanols also only display an unsatisfactory dissolving action. Therefore, the synergistic potentiation of the two essential components of the agent according to the present invention is surprising. This is shown by the following Examples and by the results given in the accompanying drawings.

As already mentioned, the process and agent according to the present invention are particularly suitable for use in conjunction with analytical determinations of serum components. By way of example, there may be mentioned triglyceride determinations with glycerol kinase as indicator system or with glycerol dehydrogenase as indicator system, Lauber's iron determination and cholesterol determinations with cholesterol oxidase and catalase or with cholesterol oxidase, phenol and 4-aminophenazone.

The following Examples are given for the purpose of illustrating the present invention:

EXAMPLES 1 TO 10

In a 1 cm. cuvette, 0.5 ml. of a serum which was very turbid due to chylomicrons was mixed at 25° C. with 1.5 ml. of an additive having the composition given in the following Table. Subsequently, the change of transmission at 546 nm was determined in dependence on the time. The results obtained are graphically illustrated in FIG. 1 of the accompanying drawings.

The agent added consisted of an aqueous solution which contained polyethylene glycol ether, alkane sulphonate and sodium toluenesulphonate in the amounts shown in the following Table. The polyethylene glycol ethers used are also described in more detail in the following Table. The alkane sulphonate used was one commercially available under the trade name "Mersolate H" which contains a mixture of secondary alkane sulphonates having 13 to 15 carbon atoms, the proportion of disulphonates being 40 to 50%.

TABLE

| Example No. | Polyethylene glycol ether | | | | amount of alkane sulphonate (%) | amount of sodium toluenesulphonate (%) |
|---|---|---|---|---|---|---|
| | (aryl)-alkanol radical | HLB value | (EO) | amount % | | |
| 1 | isotridecyl | 12 | | 6 | 4.5 | 5 |
| 2 | isooctylphenyl | 12.5 | | 6 | 4.5 | 5 |
| 3 | n-dodecyl | 13.1 | (7) | 6 | 4.5 | 5 |
| 4 | " | 14.1 | (9) | 6 | 4.5 | 5 |
| 5 | — | — | — | — | 10.5 | — |
| 6 | isotridecyl | 12 | | 10.5 | — | — |
| 7 | isooctylphenyl | 12.5 | | 10.5 | — | — |
| 8 | n-dodecyl | 13.1 | (7) | 10.5 | — | — |
| 9 | " | 14.1 | (9) | 10.5 | — | — |
| 10 | isotridecyl | 12 | | 6 | 4.6 | — |

Examples 3 to 9 are comparative Examples and are not according to the present invention.

Figure 2:
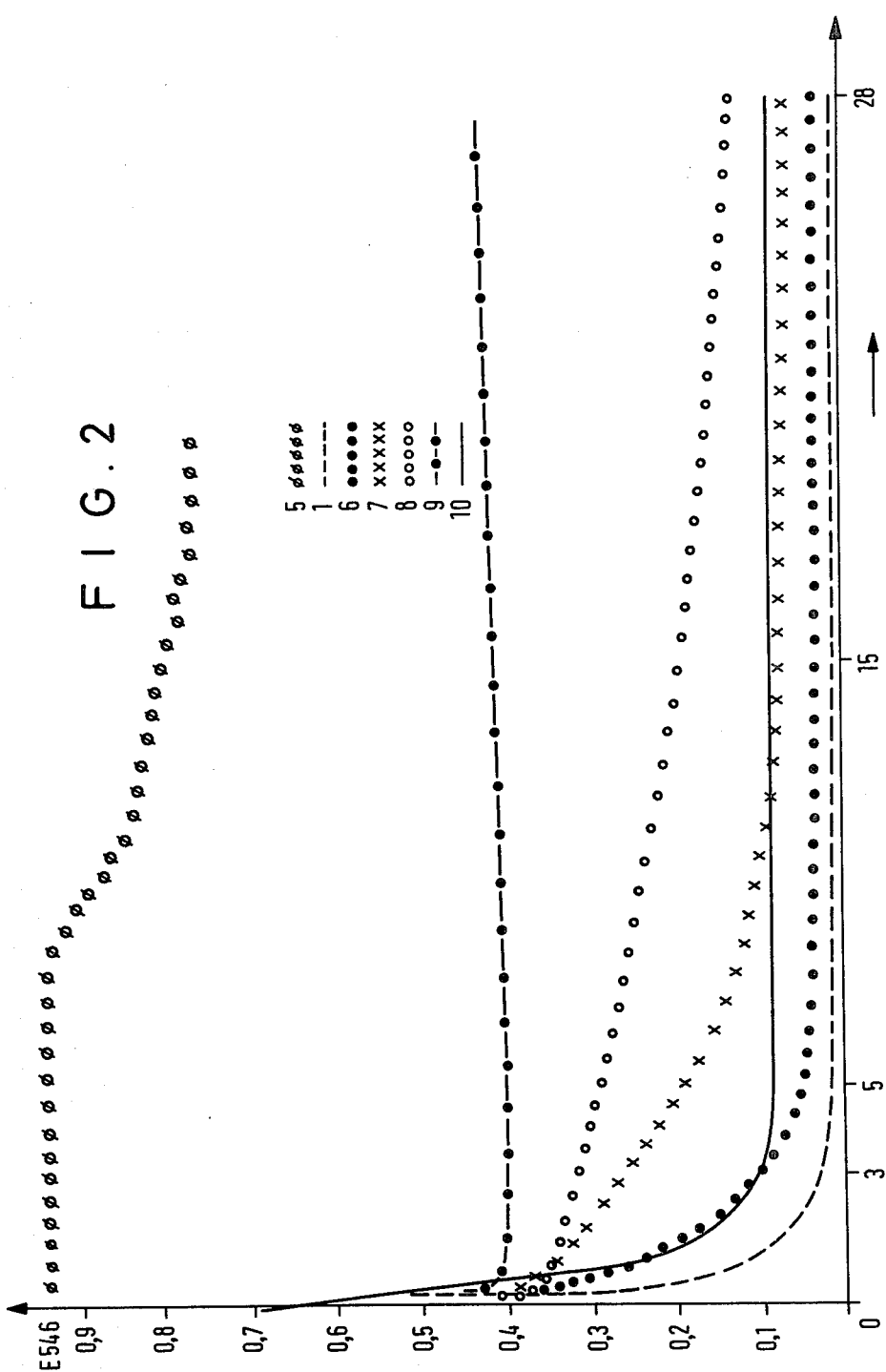

The results are illustrated in the accompanying drawings. FIG. 1 is a graphical representation of the change of transmission with time for Examples 1 to 4 and FIG. 2 is a corresponding graphical representation for Examples 5 to 10.

EXAMPLE 11

Example of use

Determination of cholesterol with cholesterol oxidase and catalase (catalase method)

In the case of this method (described in Z. Clin. Chem. Clin. Biochem., 12, 403/1974), the sample material is mixed with a reagent which consists of cholesterol oxidase, cholesterol esterase, catalase, acetylacetone, methanol and phosphate buffer (pH 7.0), as well as hydroxypolyethoxydodecane. A disadvantage of this reagent is that, in many cases, turbidities due to chylomicrons in the sample, cannot be removed and false, too low cholesterol values are obtained.

Therefore, the hydroxypolyethoxydodecane was replaced by an equal amount of the agent of Example 1. Even in the case of turbid sera, clear solutions were hereby obtained and the measured cholesterol values showed no deviations from the correct values.

What is claimed is:

1. A process for dissolving chylomicrons in an aqueous medium comprising adding to the aqueous medium in an effective amount
   (a) at least one polyethylene glycol ether of an alkanol or alkylaryl alcohol with a branched alkane chain and with an HLB value of 12 to 14, and
   (b) at least one secondary alkyl sulphonate containing 10 to 20 carbon atoms in the molecule.

2. The process of claim 1 further comprising the step of adding to the aqueous medium an alkali metal p-toluenesulphonate.

3. The process of claim 1, wherein (a) 4 to 8 parts by weight of polyethylene glycol ether and (b) 6 to 2 parts by weight of alkane sulphonate are added.

4. The process of claim 2 or 3 wherein 5 to 10% by weight of alkali metal p-toluenesulphonate, referred to the sum of (a) and (b), are added.

5. The process of claim 1 wherein a polyethylene glycol ether with an HLB value of 12.5 to 13.5 is used.

6. The process of claim 1 wherein an alkyl sulphonate containing 13 to 15 carbon atoms in the molecule is used.

7. The process of claim 2 wherein a mixture of alkyl-mono- and di-sulphonates is used.

8. The process of claim 1 or 2 wherein from about 4 to about 30% by volume of (a)+(b) are added to the aqueous medium.

9. An agent for dissolving chylomicrons in aqueous media consisting essentially of:
   (a) at least one polyethylene glycol ether of an alkanol or arylalkanol with a branched alkane chain and an HLB value of 12 to 14, and
   (b) at least one secondary alkyl sulphonate containing 10 to 20 carbon atoms in the molecule.

10. Agent of claim 9 further comprising as a viscosity modifying agent an alkali metal p-toluenesulphonate.

11. Agent of claim 10 comprising
    (a) 4 to 8 parts by weight of polyethylene glycol ether and
    (b) 6 to 2 parts by weight of alkane sulphonate.

12. Agent of claim 10 comprising 5 to 10% by weight of alkali metal p-toluenesulphonate.

13. Agent of claim 9 comprising a polyethylene glycol ether with an HLB value of 12.5 to 13.5.

14. Agent of claim 10 comprising alkyl sulphonate having 13 to 15 carbon atoms in the molecule.

15. Agent of claim 10 comprising a mixture of alkyl mono- and di-sulphonates.

* * * * *